US00PP15304P2

(12) United States Plant Patent
Warren

(10) Patent No.: US PP15,304 P2
(45) Date of Patent: Nov. 9, 2004

(54) SERVICEBERRY TREE NAMED 'JFS-ARB'

(50) Latin Name: *Amelanchier laevis*
Varietal Denomination: JFS-Arb

(75) Inventor: Keith S. Warren, Gresham, OR (US)

(73) Assignee: J. Frank Schmidt, Boring, OR (US)

( * ) Notice: Subject to any disclaimer, the term of this patent is extended or adjusted under 35 U.S.C. 154(b) by 0 days.

(21) Appl. No.: 10/627,278

(22) Filed: Jul. 25, 2003

(51) Int. Cl.[7] ..... A01H 5/00
(52) U.S. Cl. ..... Plt./216
(58) Field of Search ..... Plt./216, 156

*Primary Examiner*—Kent Bell
(74) *Attorney, Agent, or Firm*—Klarquist Sparkman LLP

(57) ABSTRACT

A variety of serviceberry which combines deep green slightly glossy foliage, upright branching, a strong straight trunk, and a straight and dominant central leader giving it an excellent tree form for use on city streets.

6 Drawing Sheets

Latin name of the genus and species of the plant claimed: *Amelanchier laevis.*
Variety denomination: 'JFS-Arb'.

BACKGROUND OF THE INVENTION

In 1990, I selected five trees of *Amelanchier laevis* from a particularly good crop of trees of this species growing in a cultivated area of a nursery in Boring, Oreg. These trees were grown from open pollinated seed of the species *Amelanchier laevis.* These five selected trees were chosen based on dormant form as being among the largest and straightest of the crop of over 1000 trees. I planted these trees in an evaluation and display area at the nursery in Boring, Oreg. I observed the growth of these trees for several years, and by 1993, it was clear that one of these five trees was distinctly straighter and more upright in form with more upright branching and a more dominant central leader. I also noticed that this one tree possessed foliage that appeared deeper green and slightly more glossy than the other four trees. At this time, I selected this single tree, 'JFS-Arb', and removed the other four trees to allow my new cultivar room to grow to mature size. As I continued to observe and evaluate this tree, I became convinced that it possessed superior characteristics that differentiated it from the species. I directed asexual propagation of this selection in small test plots at nursery growing grounds in Canby, Oreg. and Milton-Freewater, Oreg. by chip budding onto both Crataegus understock and *Amelanchier laevis* seedling understock. Observation of these propagated plants has shown that the 'JFS-Arb' cultivar reproduces true to type in successive generations of asexual reproduction. The new variety has an unusually straight trunk, a strong central leader, upright oriented branching and dark green, slightly glossy, summer foliage.

BRIEF SUMMARY OF THE INVENTION

This new cultivar possesses a unique combination of characteristics in that it combines an unusually straight trunk, a strong central leader, upright oriented branching, and deep green, slightly glossy foliage.

BRIEF DESCRIPTION OF THE DRAWING

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
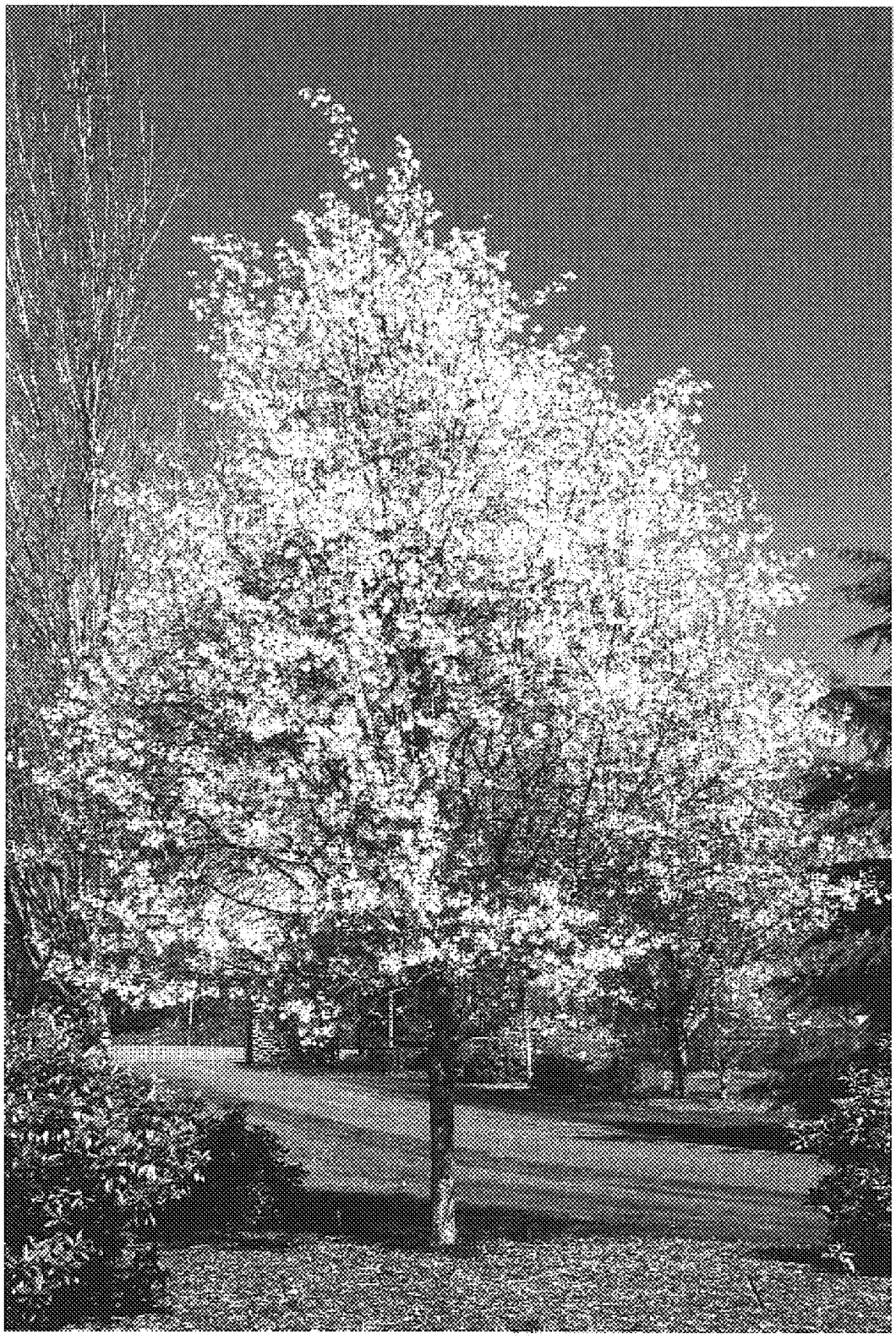
FIG. 1 is a photograph of a tree of my new variety in full flower.
Figure 2:
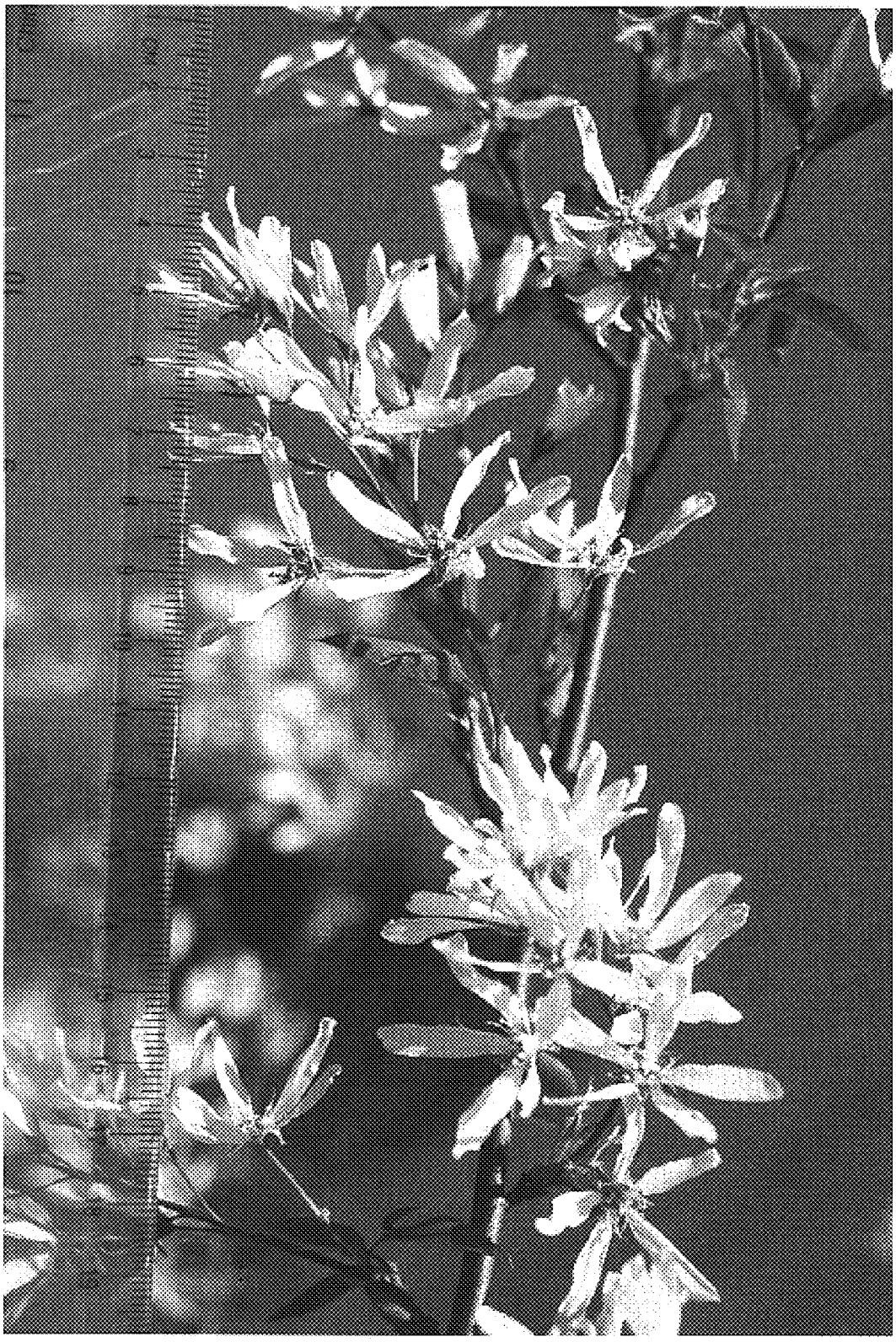
FIG. 2 is a close up of a portion of a flowering branch of a tree of my new variety.
Figure 3:
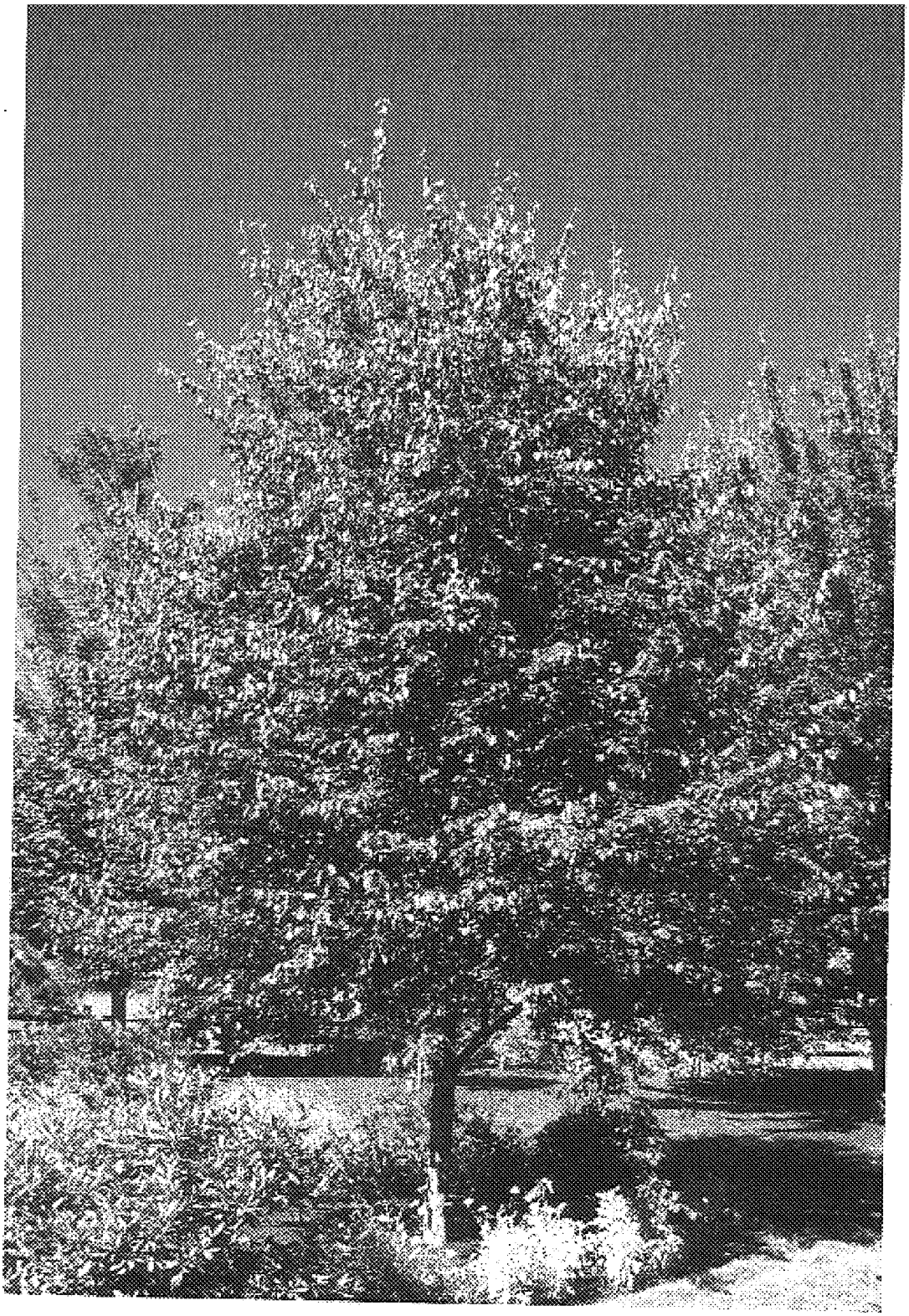
FIG. 3 is a photograph of a tree of my new variety in summer foliage.
Figure 4:
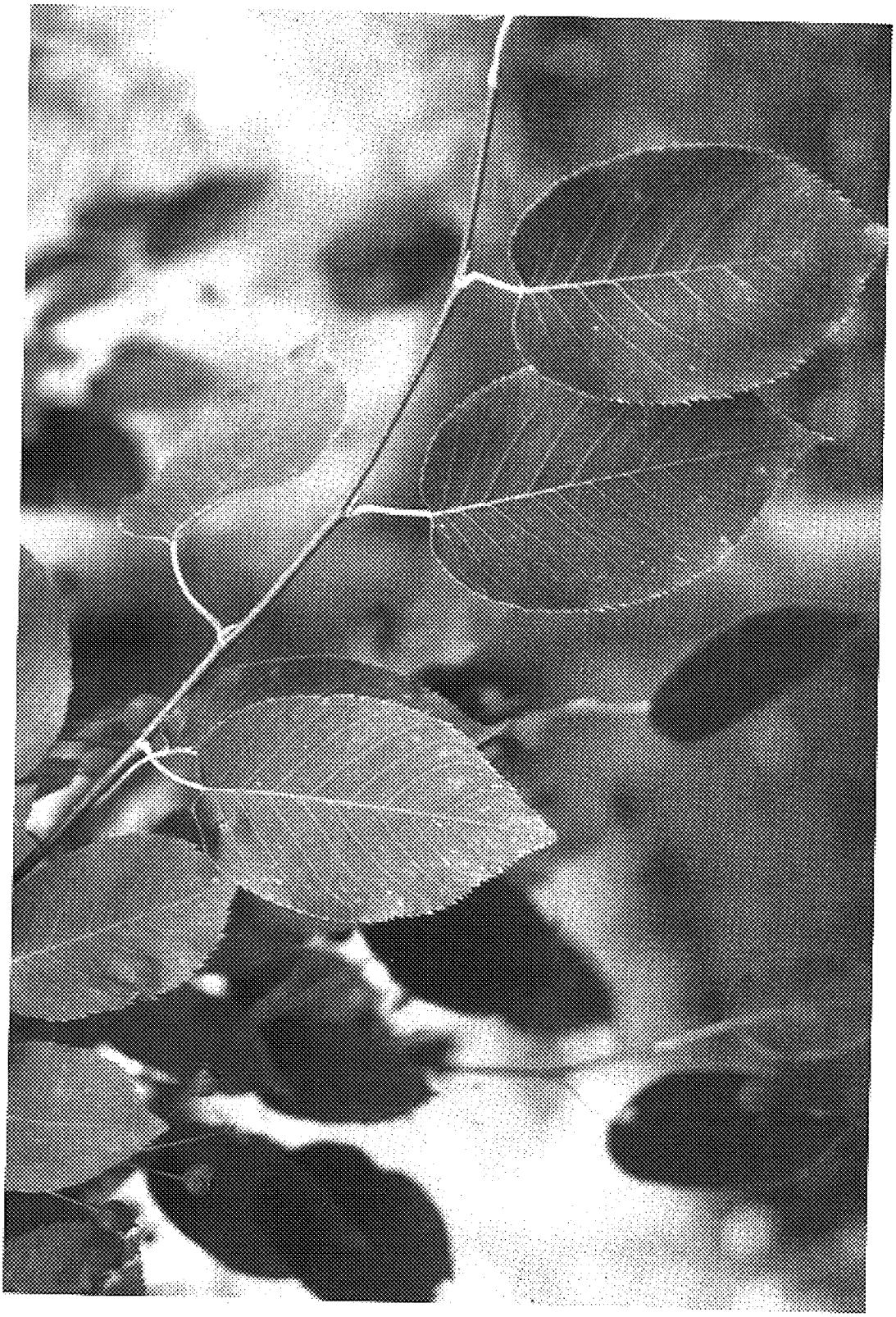
FIG. 4 is a close up of a branch of my new variety showing leaves with their green foliage color and also illustrating some immature fruit.
Figure 5:
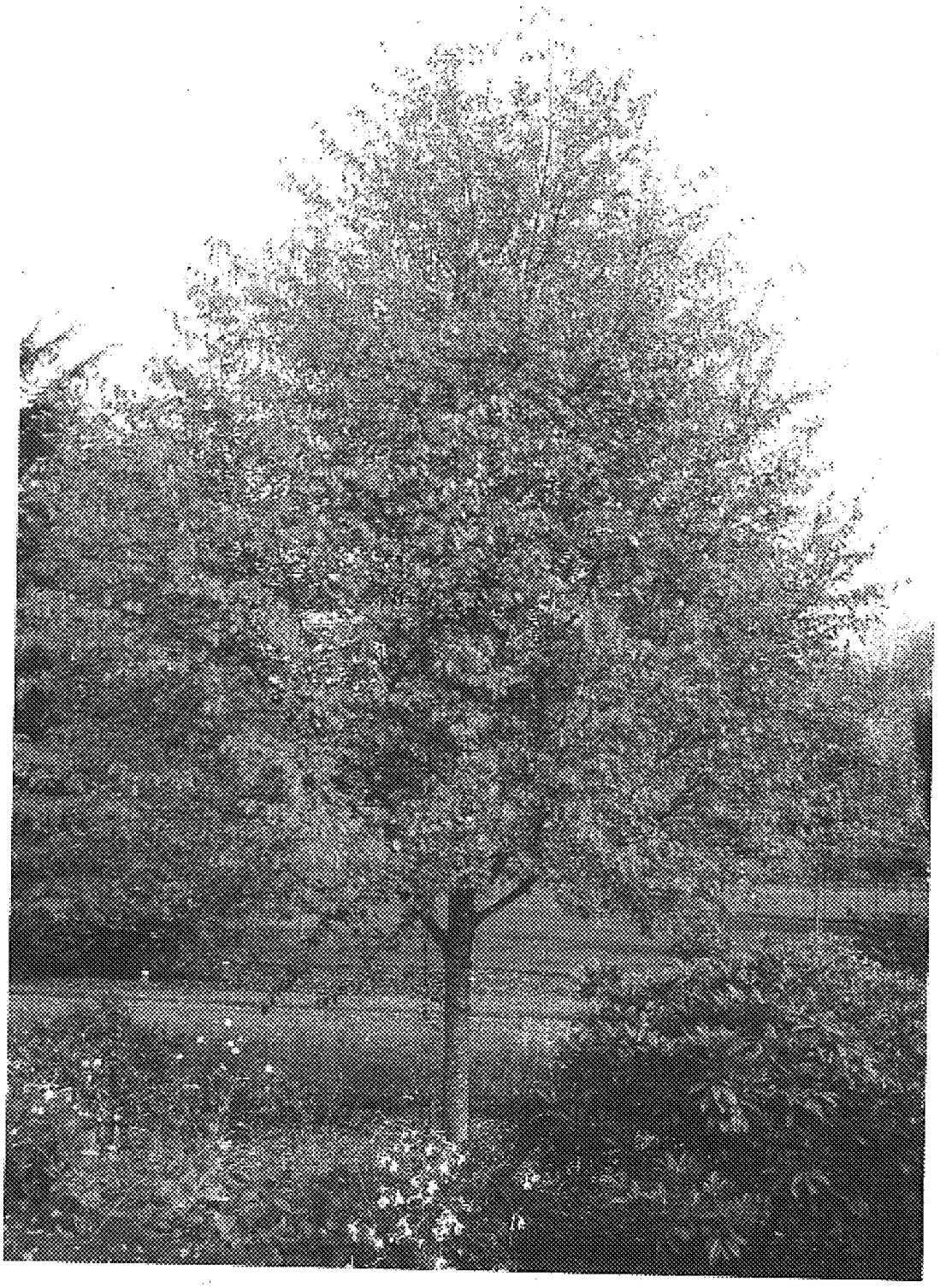
FIG. 5 is a photograph of a tree of my new variety with foliage in fall color.
Figure 6:
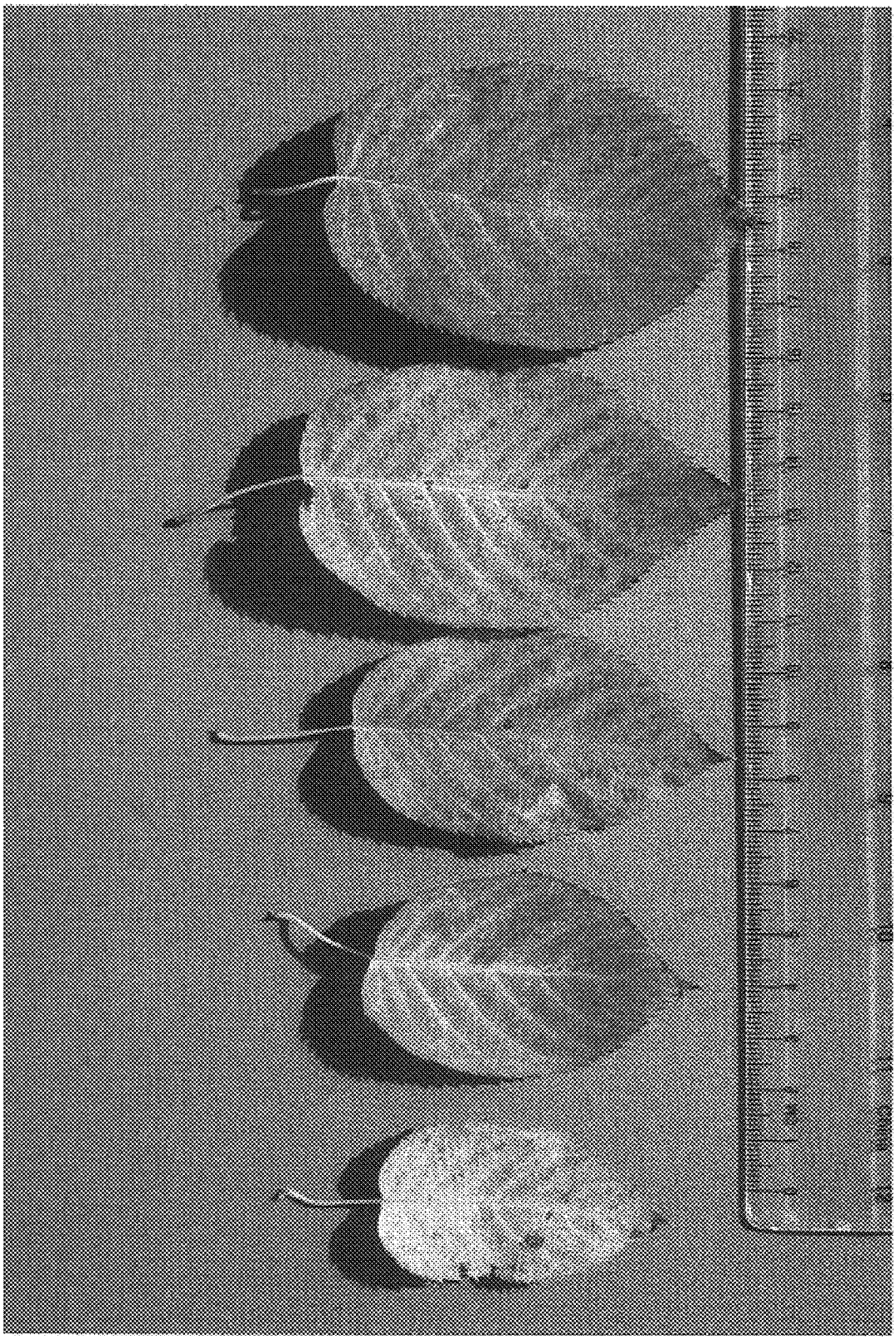
FIG. 6 is a close up of some leaves of a tree of my new variety in fall color.

The following detailed description of the 'JFS-Arb' variety is based on observations of the original tree growing in Boring, Oreg. and of two year old asexually reproduced progeny. The observed progeny were trees which were growing in Canby, Oreg. and Milton-Freewater, Oreg.

Scientific name: *Amelanchier laevis* 'JFS-Arb'.
Parentage:
- *Seed parent.*—An unnamed tree of *Amelanchier laevis.*
- *Pollen parent.*—Unknown, believed to be an unnamed tree of *Amelanchier laevis.*

Tree:
- *Overall shape.*—Upright, oval with pointed crown.
- *Height.*—Original tree at about 16 years of age, about 8.5 meters high.
- *Width.*—Original tree at about 16 years of age, about 6.0 meters spread.
- *Caliper.*—Original tree at about 16 years of age, 19.3 cm measured 1 meter above the ground. A group of two year old trees average 27 mm, when measured 15 cm above the ground.
- *Trunk.*—Strong and straight under outdoor nursery growing conditions.
- *Trunk bark texture.*—Smooth with sparse, low lenticels.

*Trunk bark color.*—Immature bark color: Greyed-green (RHS 196A to 197B) on 2 year old trees. Mature bark color: Greyed-green (RHS 197C) on 16 year old original tree. Lenticels: Oval to elongated oval, become stretched or elongated in the horizontal direction as trunk grows, rather sparse and not prominent. They stretch until no longer apparent. Variable in size, an exemplary tree with 25 mm caliper trunk had lenticels about 1 mm vertical dimension and about 2.5 mm horizontal dimension. Lenticels were greyed-orange (RHS 164B) in color.

*Primary branches.*—Upright growth habit; forming an upright oval shaped crown. At about 16 years of age, the primary branches on the original tree varied from 4.5 m to 6.0 m in length and 7.8 cm to 10.5 cm in diameter at their bases; they averaged 5.4 m in length and 9.2 cm in diameter.

*Branch color.*—Color of one year old branches varies from the tip to the base. Measured during the dormant season, one year old branches are greyed-orange (RHS 174A) near the tip, greyed-orange (RHS 174B) in the mid-section, and grey-brown (RHS 199B) at the base.

*Branch lenticels.*—Similar to trunk, horizontal in orientation, oval to elongated oval, greyed-orange (RHS 164B) in color.

*Dormant buds.*—Long, narrowly acute to lanceolate, yellow-green in color (RHS 146B), with imbricate scales. Typical terminal buds averaged 18 mm long by 4 mm wide; typical lateral buds are 8–15 mm (averaged 12 mm) long by 3 mm wide. Buds are nearly glabrous except ciliate with white hairs at edges of scales.

*Internodes.*—Moderately fast growing, average internode length of a sample of trees was about 31 mm on a one-year old shoot.

*Hardiness.*—Not determined, observed in USDA Hardiness Zones 6 and 8. No cold damage has been observed under these conditions.

*Disease resistance.*—Resistance to powdery mildew and rust is somewhat improved over that typical of the species, but is not complete.

Leaves: Except as otherwise noted, observations are from twenty vigorous growth leaves.

*Arrangement.*—Alternate.

*Texture.*—Smooth.

*Sheen.*—Slightly glossy.

*Length.*—Averaged 68 mm, measured on original tree.

*Width.*—Averaged 42 mm, measured on original tree.

*Petioles.*—Length varied from 13 to 26 mm, width 2 mm. Color is Yellow-green (RHS 145B) with a spotty overtone of greyed-purple (RHS 183B).

*Overall shape.*—Ovate to elliptic-ovate.

*Margin.*—Finely serrate. Each serration 1–2 mm high by 2–3 mm wide at base.

*Tip.*—Acute.

*Base.*—Generally shallowly cordate, with some leaves varying to slightly rounded.

*Stipules.*—None.

*Spring leaf color, first emerging leaves.*—Greyed-orange (RHS 176B to 176D).

*Summer leaf color.*—Upper leaf surface: Green (RHS 139A to 139B), slightly glossy. Lower leaf surface: Yellow-green (RHS 148B). Vein: Green (RHS 143B).

*Fall leaf color.*—Fall leaf colors are a mix of Yellow-orange (RHS 23A) and Greyed-red (RHS 179A). When the tree is viewed from a distance, this mix gives an overall tree color appearance of Orange-red (RHS 31A).

*Pubescence.*—None, glabrous.

*Persistence.*—Tree is deciduous.

Flowers: Observations are from representative flower samples observed in Boring, Oreg.

*Overall.*—Perfect, held in slightly elongated, semi-pendulous 8–13 cm long racemes of 8–12 flowers.

*Shape.*—Elongated, with lax petals at first, then petals flare to a rounded shape at anthesis.

*Size.*—Flowers average 15 mm wide after emerging from bud, then petals reflex, expanding the flower to 46 mm in diameter. Flower depth averages 18 mm when flowers first open, then as the petals reflex, the flowers flatten until they average only 5 mm deep.

*Flower buds.*—Unopened dormant buds are long, narrowly acute to lanceolate, with imbricate scales. Terminal dormant buds averaged 18 mm long by 4 mm wide; lateral buds were 8–15 mm (averaged 12 mm) long by 3 mm wide. Dormant buds are glabrous, except for ciliate bud scale margins. As buds open, a tomentum is exposed on the inner surface of the bud scales. As the flower raceme expands from the bud, eight to twelve individual flower buds expand to 10 mm long by 4 mm wide before opening into flowers.

*Color.*—Unopened buds: Yellow-green in color (RHS 146B). Opened flower: Petals are white (RHS 155D), the caylx is green (RHS 143B).

*Petals.*—Five petals per flower; 21 mm long; 4 mm wide. Petals are long oblanceolate to strap-shaped, with a rounded apex, an acute base, and smooth margins.

*Sepals.*—Five sepals per flower, green (RHS 143B). Sepals acute, 2 mm long, 1 mm wide. The sepal margin is smooth and heavily covered with a fine pubescence.

*Stamen.*—About twenty stamens, length 4 to 5 mm long, arranged concentrically around pistil, attaching to edge of hypanthium.

*Anthers.*—Yellow in color, (RHS 11D) 1 mm long, ovoid.

*Pistil.*—One pistil per flower. Length about 5 mm, stigma separated into five branches over one-half of its length. Ovary inferior, five syncarpous carpels, two ovules per carpel.

*Hypanthium.*—Campanulate, 5 mm wide, green (RHS 143A).

*Pollen.*—Yellow (RHS 12C).

*Pedicel.*—10–35 mm in length, depending on the position on the raceme, with longer pedicels at the base of raceme. 0.8 mm in width, color is yellow-green (RHS 146A to 152B).

*Peduncle.*—8 to 12 mm long, 1 to 2 mm wide, color is composed of a cast of greyed-purple (RHS 183A) over a base color of yellow-green (RHS 146A). Under cool, cloudy weather conditions at the time of bloom, the greyed-purple color cast is very noticeable, but is insignificant under warm sunny conditions.

*Pubescence.*—Flower parts are all glabrous.

*Fragrance.*—Extremely faint, slightly earthy.

*Flowering date.*—In Boring, Oreg. (2003 data). First bloom Apr. 4, 2003; Peak bloom Apr. 10, 2003, End of bloom Apr. 19, 2003. Individual flowers last an average of 10 days under typical conditions in Boring, Oreg.

Fruit: Observations are from a sampling of typical fruit.

*Size.*—Typical fruit average 9 mm diameter.

*Shape.*—Globose, pome, fleshy.

*Cavity.*—None.

*Basin.*—None.

*Skin.*—Smooth.

*Lenticels.*—None observed.

*Color.*—Red (RHS 53C) when immature, ripening to greyed-purple (RHS 187A).

*Seeds.*—Up to 10, but generally 2 to 7 per fruit, shape reniform.

*Fruit production.*—Moderately prolific.

*Usage.*—Edible, sweet, ornamental. Of wildlife value as they are favored by birds.

Comparison to other varieties:

Comparison to most similar cultivar, 'Majestic' U.S. Plant Pat. No. 7,203

| Feature | 'JFS-Arb' | 'Majestic' |
|---|---|---|
| Petal dimensions: | 21 mm × 4 mm | 18 mm × 7 mm |
| Petal shape: | Elongated, strap shaped | Oblong-oval |
| Flower date (2003) | 4/4, first bloom<br>4/10, peak bloom<br>4/19, last bloom | 4/11, first bloom<br>4/19, peak bloom<br>4/25, last bloom |
| Calyx color: | Green (RHS 143B) | Greyed-purple (183B) |
| Leaf color: earliest emerging | Greyed-orange (RHS 176B to 176D) | Greyed-red (RHS 178B to 181B) |

Comparison to the species, *Amelanchier laevis:* 'JFS-Arb' differs from typical *Amelanchier laevis* seedlings by faster growth as a one year old nursery tree, glossier foliage, a narrower branch angle, and a significantly straighter leader.

| Feature | 'JFS-Arb' | *A. laevis* seedlings |
|---|---|---|
| Nursery height, 1 year | | |
| Measured 6/11/01 | 95.6 cm | 67.2 cm |
| Measured 10/1/01 | 195.4 cm | 153.5 cm |
| Summer leaf gloss | Slightly glossy | Dull |
| Leader straightness | 3° from vertical | 17° from vertical |
| Top of 2 year trees | | |
| Branch angle, 5 year trees 50 cm from trunk | 35.5° from vertical (10 branches averaged) | 58.5° from vertical (20 branches from four trees averaged) |

I claim:

1. A new and distinct variety of serviceberry tree, substantially as herein shown and described.

* * * * *